United States Patent
Dempsey et al.

(10) Patent No.: US 9,423,477 B2
(45) Date of Patent: *Aug. 23, 2016

(54) SPLIT MAGNETIC RESONANCE IMAGING SYSTEM

(71) Applicant: ViewRay Incorporated, Oakwood Village, OH (US)

(72) Inventors: James F. Dempsey, Chagrin Falls, OH (US); John L. Patrick, Chagrin Falls, OH (US); Shmaryu M. Shvartsman, Highland Heights, OH (US); Gordon D. DeMeester, Wickliffe, OH (US)

(73) Assignee: ViewRay Technologies, Inc., Oakwood Village, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/452,416

(22) Filed: Aug. 5, 2014

(65) Prior Publication Data

US 2014/0347053 A1 Nov. 27, 2014

Related U.S. Application Data

(63) Continuation of application No. 13/034,377, filed on Feb. 24, 2011, now Pat. No. 8,803,524.

(60) Provisional application No. 61/307,665, filed on Feb. 24, 2010.

(51) Int. Cl.
*G01R 33/38* (2006.01)
*G01R 33/385* (2006.01)
(Continued)

(52) U.S. Cl.
CPC .......... *G01R 33/3802* (2013.01); *A61B 5/055* (2013.01); *G01R 33/3806* (2013.01); *G01R 33/3856* (2013.01); *G01R 33/4808* (2013.01); *A61N 2005/1055* (2013.01)

(58) Field of Classification Search
CPC .......... G01R 33/3856; G01R 33/3806; G01R 33/4808; G01R 33/3802; A61N 2005/1055; A61B 5/055

USPC ......... 324/318, 321, 322; 600/411; 335/216, 335/296

See application file for complete search history.

(56) References Cited

U.S. PATENT DOCUMENTS 3,851,729 A 12/1974 Gordon
5,291,169 A 3/1994 Ige et al.
(Continued)

FOREIGN PATENT DOCUMENTS

EP 0332176 A2 9/1989
EP 0424808 A1 5/1991
(Continued)

OTHER PUBLICATIONS

Lagendijk J. J. et al. "MRI guided radiotherapy: A MRI based linear accelerator." Radiotherapy & Oncology. vol. 56, No. Supplement 1. Sep. 2000. S60-S61. XP008012866. 19th Annual Meeting of the European Society for Therapeutic Radiology and Oncology. Istanbul, Turkey; Sep. 19-23, 2000.
(Continued)

*Primary Examiner* — Melissa Koval
*Assistant Examiner* — Rishi Patel
(74) *Attorney, Agent, or Firm* — Mintz Levin Cohn Ferris Glovsky and Popeo, P.C.

(57) ABSTRACT

A magnetic resonance imaging (MRI) system includes a split magnet system having a pair of MRI magnet housings separated by gap. A pair of main MRI magnets are disposed within respective MRI magnet housings. A plurality of buttress assemblies are attached to the MRI magnet housings. Some or all of the buttress assemblies are provided with removable connections to the MRI magnet housings. This allows for partial disassembly of the MRI system for improved transport and maneuverability for relocating the MRI system. The MRI system can include a gantry in the gap for supporting a radiation therapy system. Also, the removably buttress assemblies can be used for housing conduits, such as electrical and fluid conduits, between the pair of MRI magnet housings.

20 Claims, 7 Drawing Sheets

(51) Int. Cl.
    *A61B 5/055*     (2006.01)
    *G01R 33/48*     (2006.01)
    *A61N 5/10*     (2006.01)

(56) References Cited

U.S. PATENT DOCUMENTS

| | | |
|---|---|---|
| 5,363,077 A | 11/1994 | Herd et al. |
| 6,289,681 B1 | 9/2001 | Eckels et al. |
| 6,437,672 B1 | 8/2002 | Takeshima et al. |
| 6,570,475 B1 | 5/2003 | Lvovsky et al. |
| 7,646,199 B2 | 1/2010 | Dannels et al. |
| 7,646,272 B1 | 1/2010 | Schmierer et al. |
| 8,639,006 B2 | 1/2014 | Dempsey et al. |
| 8,803,524 B2 | 8/2014 | Dempsey et al. |
| 8,929,638 B2 | 1/2015 | Dempsey et al. |
| 8,952,346 B2 | 2/2015 | Dempsey et al. |
| 2002/0087064 A1 | 7/2002 | Tsuda |
| 2004/0021538 A1 | 2/2004 | Watanabe et al. |
| 2005/0197564 A1 | 9/2005 | Dempsey |
| 2007/0210798 A1 | 9/2007 | Race et al. |
| 2009/0149735 A1 | 6/2009 | Fallone et al. |
| 2009/0299170 A1 | 12/2009 | Gebhardt et al. |
| 2010/0033186 A1 | 2/2010 | Overweg et al. |
| 2010/0322497 A1 | 12/2010 | Dempsey et al. |
| 2011/0012593 A1 | 1/2011 | Shvartsman et al. |
| 2011/0121832 A1 | 5/2011 | Shvartsman et al. |
| 2011/0213239 A1 | 9/2011 | Amies et al. |
| 2012/0022363 A1 | 1/2012 | Dempsey |
| 2013/0147476 A1 | 6/2013 | Shvartsman et al. |
| 2013/0245425 A1 | 9/2013 | Dempsey |
| 2013/0296687 A1 | 11/2013 | Dempsey |
| 2014/0121495 A1 | 5/2014 | Dempsey |
| 2014/0263990 A1 | 9/2014 | Kawrykow et al. |
| 2014/0266206 A1 | 9/2014 | Dempsey et al. |
| 2014/0266208 A1 | 9/2014 | Dempsey et al. |
| 2014/0275963 A1 | 9/2014 | Shvartsman et al. |
| 2014/0330108 A1 | 11/2014 | Dempsey |

FOREIGN PATENT DOCUMENTS

| | | |
|---|---|---|
| JP | H01-227407 A | 9/1989 |
| JP | H03-205029 A | 9/1991 |
| JP | H10-127602 A | 5/1998 |
| JP | 2002102198 A | 4/2002 |
| JP | 2002102198 A | 4/2002 |
| JP | 2004-267526 A | 9/2004 |
| JP | 2005-150245 A | 6/2005 |
| JP | 2008-212667 A | 9/2008 |
| WO | WO-03/008986 A2 | 1/2003 |

OTHER PUBLICATIONS

Raaymakers et al. "Integrating a 1.5 T MRI scanner with a 6 Mv accelerator: proof of concept". May 19, 2009. Physics in Medicine and Biology. vol. 54 No. 12, N229-N237.

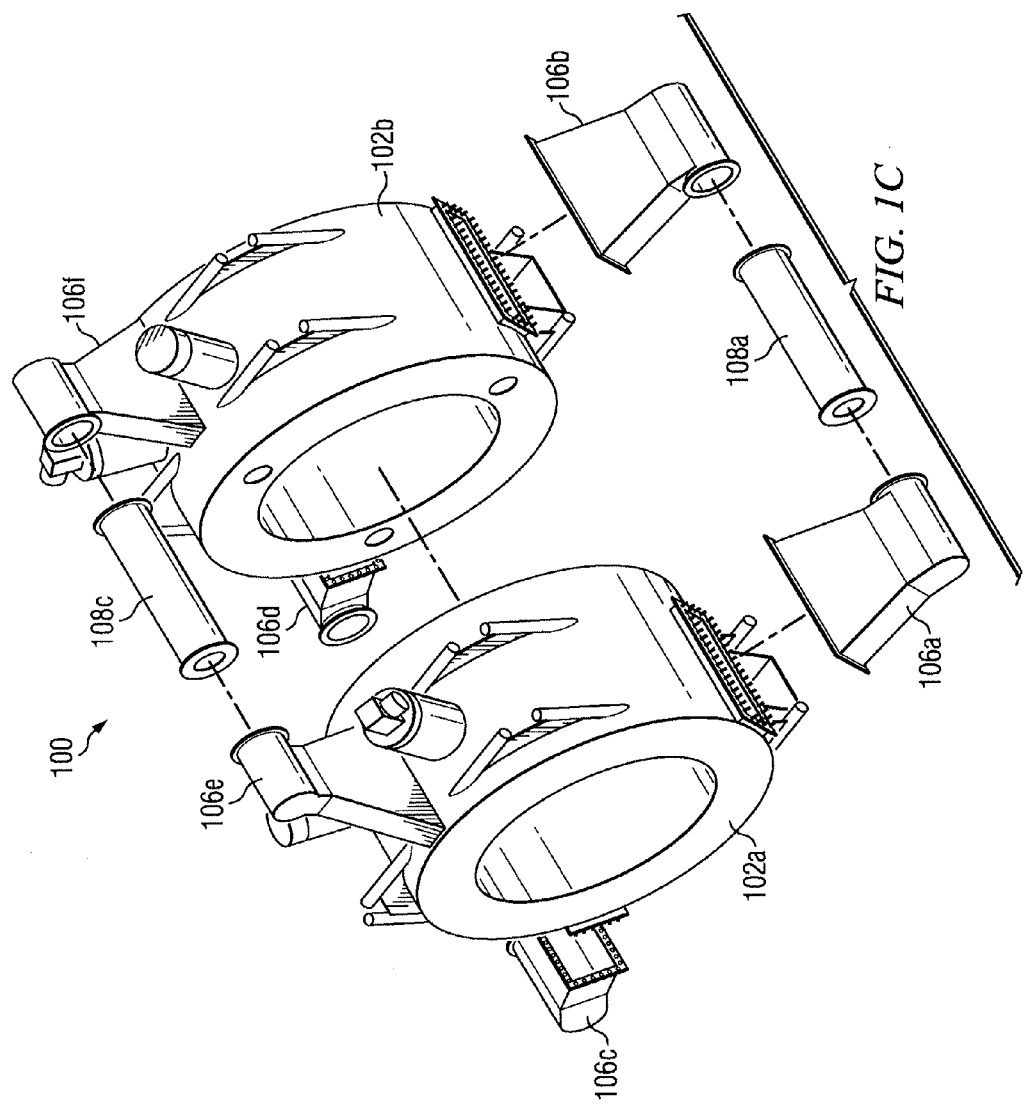

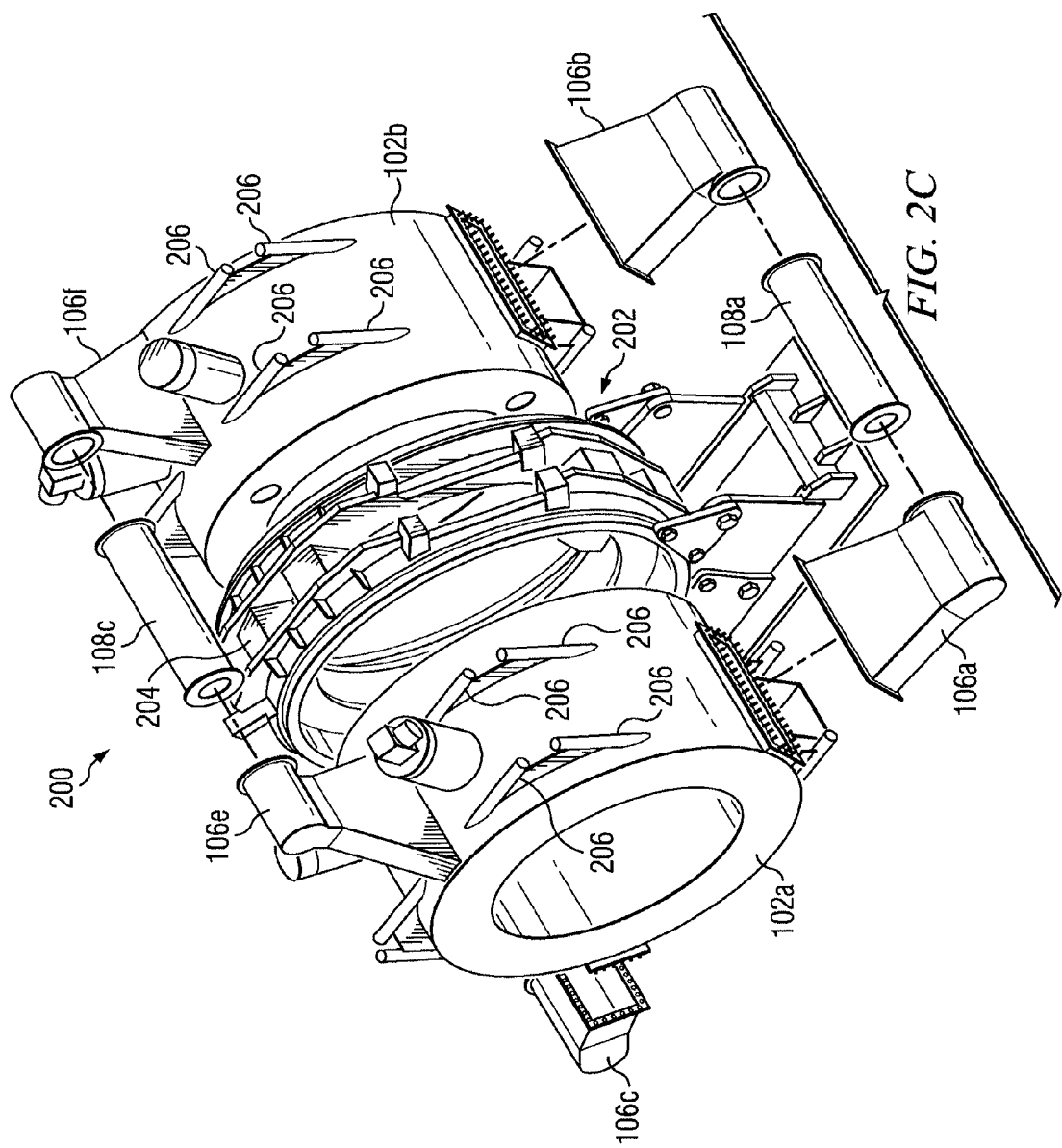

SPLIT MAGNETIC RESONANCE IMAGING SYSTEM

REFERENCE TO PRIORITY DOCUMENTS

This application is a continuation of U.S. application Ser. No. 13/034,377, filed Feb. 24, 2011, entitled "Split Magnetic Resonance Imaging System," now U.S. Pat. No. 8,803,524 issued on Aug. 12, 2014, which claims the benefit of U.S. Provisional Application No. 61/307,665, filed Feb. 24, 2010, entitled "Split MRI System." The priority of the filing dates and disclosures of each of the above-mentioned patent applications are hereby incorporated by reference in their entirety.

BACKGROUND

1. Technical Field

The present application relates to magnetic resonance imaging (MRI) systems, particularly MRI systems that include a split main magnet.

2. Related Art

Magnetic Resonance Imaging (MRI), or nuclear magnetic resonance imaging (NMRI), is primarily a medical imaging technique most commonly used in radiology to visualize the internal structure and function of the body. MRI is described, for example, by E. MARK HAACKE ET AL., MAGNETIC RESONANCE IMAGING: PHYSICAL PRINCIPLES AND SEQUENCE DESIGN (Wiley-Liss 1999), which is hereby incorporated herein by reference. A variety of MRI systems are known and are in wide use today. However, such systems typically include large components, making them difficult to move and install, especially in an existing space where access points such as available doors and hallways provide for limited maneuverability.

As will therefore be appreciated, there exists advantages to improving MRI systems so as to make such systems easier to move and install, without sacrificing the quality of the MRI system's functionality.

SUMMARY

Disclosed herein is an MRI system having a split MRI configuration that can more easily be relocated and installed compared to prior split MRI systems. The disclosed MRI system is preferably constructed so that it can be disassembled, moved, and then installed into existing facilities and shielded vaults.

Aspects of the present disclosure include a magnetic resonance imaging (MRI) system comprising first and second MRI magnet housings separated by an MRI magnet gap, with a first main MRI magnet disposed within the first MRI magnet housing and a second main MRI magnet disposed within the second MRI magnet housing. A plurality of buttress assemblies and/or their sub-assemblies are attached to the first and second MRI magnet housings. At least one of the plurality of buttress assemblies and/or sub-assemblies is removably attached to at least one of the first and second MRI magnet housings.

In some embodiments, at least one of the plurality of buttress assemblies can be removably attached to both the first and second MRI magnet housings.

In some embodiments, at least one of the plurality of buttress assemblies can include a first buttress sub-assembly that is attached to the first MRI magnet housing, and a second buttress sub-assembly that is attached to the second MRI magnet housing. In such embodiments, the buttress assembly can further include a central buttress connector that is removably connected to first and second buttress sub-assemblies. Also, in such embodiments the first buttress sub-assembly can extend radially from an outer surface of the first MRI magnet housing when attached thereto, and the second buttress sub-assembly can extend radially from an outer surface of the second MRI magnet housing when attached thereto.

In some embodiments, the MRI system can further comprise a gantry positioned in the MRI magnet gap. A radiation therapy device or other interventional therapeutic device can be supported by the gantry.

In some embodiments, the MRI system can further comprise a cooling system, which can include fluid conduit for carrying coolant for cooling the first and second main MRI magnets. The fluid conduit can extend from within the first MRI magnet housing to within the second MRI magnet housing via at least one of the removably attached buttress assemblies.

In some embodiments, the MRI system can further comprise a power system, which can include electrical conduit for providing electrical power to the first and second main MRI magnets. The electrical conduit can extend from within the first MRI magnet housing to within the second MRI magnet housing via at least one of the removably attached buttress assemblies.

The first and second MRI magnet housings can be substantially cylindrical, allowing for accommodating a patient bed within the MRI system for supporting a patient undergoing MRI imaging and/or other medical treatment involving the MRI system.

BRIEF DESCRIPTION OF THE DRAWINGS

Features, aspects, and embodiments of the inventions are described in conjunction with the attached drawings, in which:

FIGS. 1A-1C show perspective views of a first embodiment of a split-magnet MRI system;

FIGS. 2A-2C show perspective views of a second embodiment of a split-magnet MRI system.

DETAILED DESCRIPTION

Figure 1A:
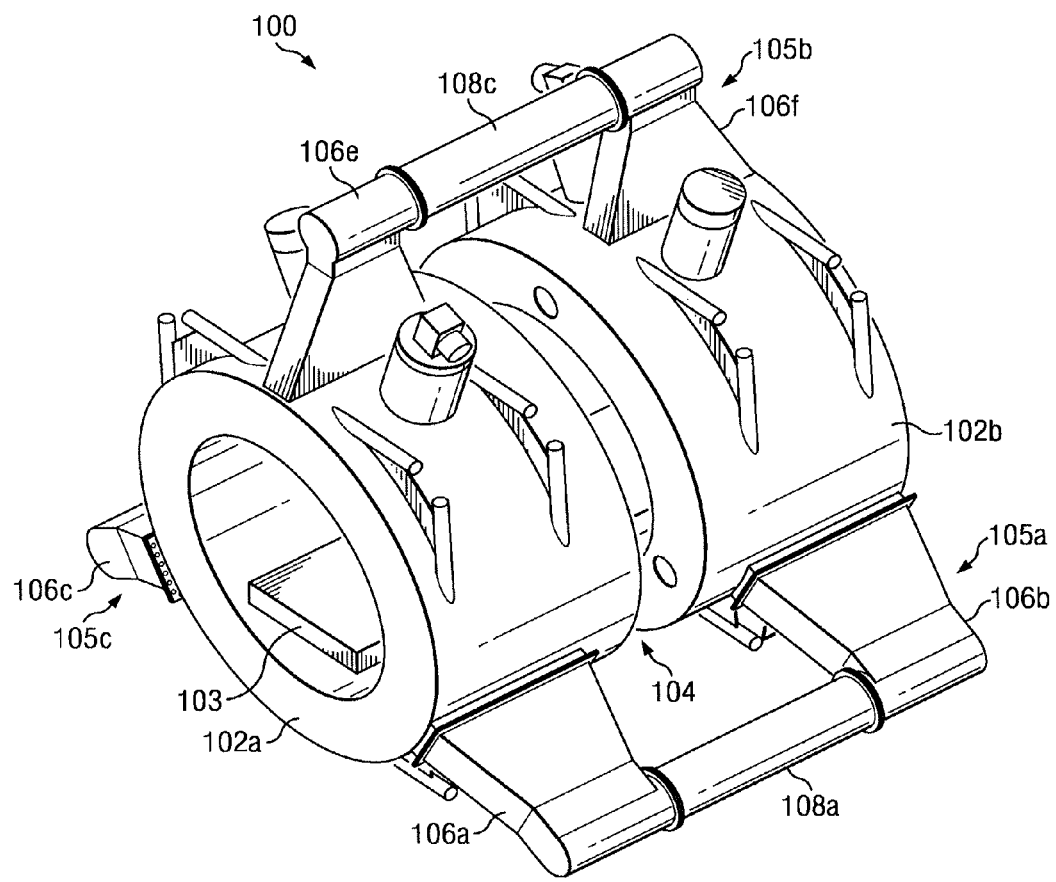
Figure 1B:
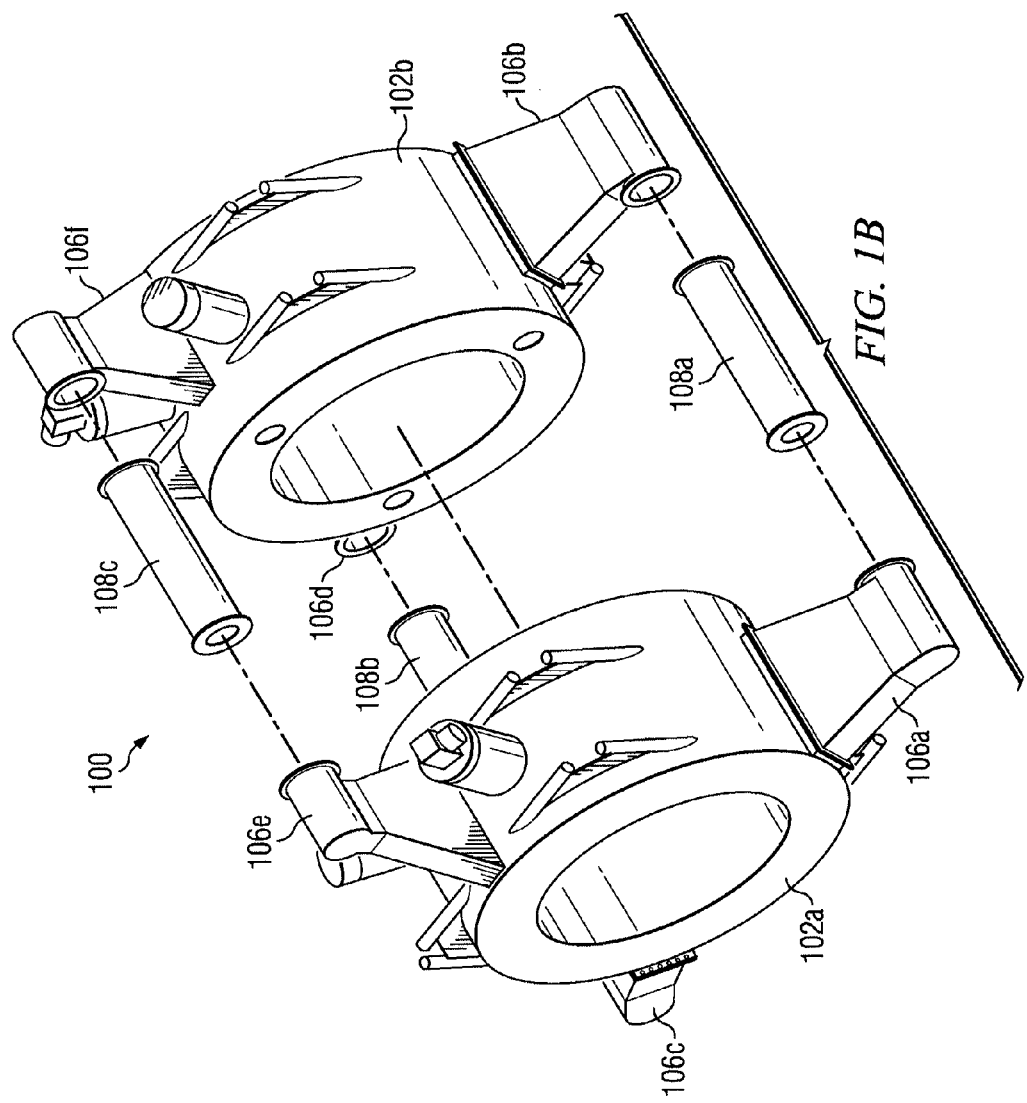

FIGS. 1A through 1C show perspective views of a split-magnet MRI system 100. FIGS. 1A shows a fully assembled view of the MRI system 100, FIG. 1B shows a partially exploded view of the MRI system 100, and FIG. 1C shows a further exploded view of the MRI system 100.

The MRI system 100 has a split MRI configuration that can more easily be relocated and installed compared to prior MRI systems. The disclosed MRI system 100 is preferably constructed so that it can be disassembled, moved, and then installed into existing facilities and shielded vaults. The MRI system 100 includes first and second cylindrical main MRI magnet housings 102a and 102b for housing respective cylindrical superconducting MRI main magnets 101a and 101b, respectively (shown in FIG. 3). The MRI main magnets 101a and 101 b can be operated to produce a uniform magnetic field in a Field-of-View (FOV) for imaging that is generally centered in a gap 104 between the two magnet housings 102a and 102b for imaging a patient positioned on patient bed 103. The MRI main magnet housings 102a and 102b are supported and connected to each other by buttress assemblies 105a-105c. According to various embodiments, the buttress assemblies 105a-105c can connect the MRI main magnets 101a and 101b mechanically, thermally, and/or electronically to improve the performance of the MRI main magnets 101a and 101b and withstand the forces between the main magnets 102a and 102b.

Buttress assemblies 105a-105c include buttress sub-assemblies 106a-106f, which extend radially out from the magnet housings 102a and 102b, and buttress connectors 108a-108c, which connect respective pairs of the buttress sub-assemblies 106a-106f. More specifically, buttress assembly 105a includes buttress sub-assemblies 106a and 106b connected by buttress connector 108a; buttress assembly 105b includes buttress sub-assemblies 106c and 106d connected by buttress connector 108b; and buttress assembly 105c includes buttress sub-assemblies 106e and 106f connected by buttress connector 108c.

As best shown in FIGS. 1B and 1C, the buttress sub-assemblies 106a-106d of buttress assemblies 105a and 105b are removable from the magnet housings 102a and 102b, while buttress sub-assemblies 106e and 106f are permanently attached to magnet housings 102a and 102b. However, all three of the buttress connectors 108a-108c are removable from respective buttress sub-assemblies 106a-106f.

The buttress sub-assemblies 106a-106d are removably connected to magnet housings 102a and 102b using known removable connection devices, such as known connection hardware that can include, for example, screws and/or nuts and bolts. In contrast, the buttress sub-assemblies 106e and 106f are permanently attached to the magnet housings 102a and 10b, respectively. For example, the buttress sub-assemblies 106e and 106f can be welded to the respective magnet housings 102a and 102b, or alternatively attached using adhesives or other permanent attachment means.

The buttress connectors 108a-108c are removably connected to respective pairs of buttress sub-assemblies 106a-106f using known removable connection devices, such as known connection hardware that can include, for example, screws or nuts and bolts. While the illustrated embodiment includes three buttress assemblies 105, of which two include pairs of removable buttress sub-assemblies 106, this is merely one of many possible embodiments. Alternative embodiments can include n buttress assemblies 105, where n can be any integer greater than or equal to 2, and where any number from 2 to n of the buttress assemblies 105 can include at least one removable buttress sub-assembly 106. In other words, alternative embodiments can include any number of buttress assemblies 105, some or all of which can include at least one removable buttress sub-assembly 106. The determination as to whether to construct the buttress sub-assemblies 106 to be removably attached to a housing 102 or permanently attached to a housing 102 can be based on achieving a balance among such factors as portability and ease of installation. By making buttress sub-assemblies 106 removable, the MRI system 100 can be disassembled into components that are more portable than the fully assembled MRI system 100. On the other hand, removable assemblies can add to the steps required for final assembly, so it may be desirable to permanently attach at least some buttress sub-assemblies, such as buttress sub-assemblies 106e and 106f, while making the remaining buttress sub-assemblies 106a-106d removable for improved portability.

For example, removing laterally-extending buttress sub-assemblies 106a and 106c may allow for the MRI housing 102a and the remaining upwardly-extending buttress sub-assembly 106e to be more easily moved through hallways and doorways of existing structures.

Figure 2A:
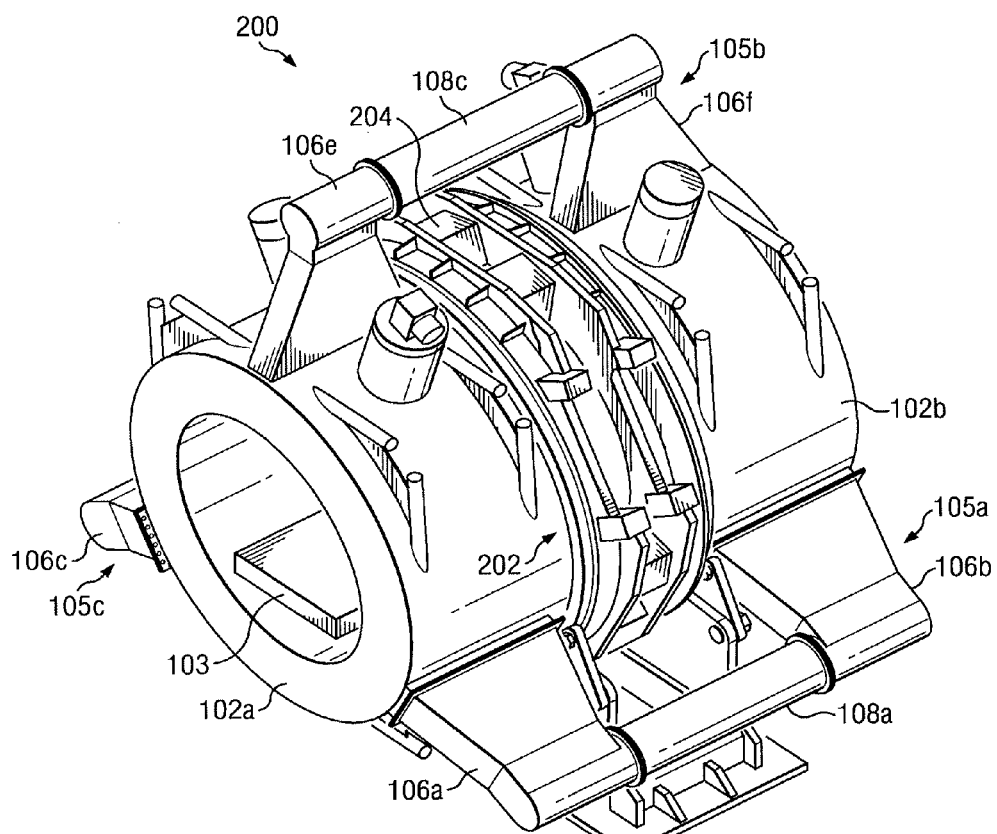
Figure 2B:
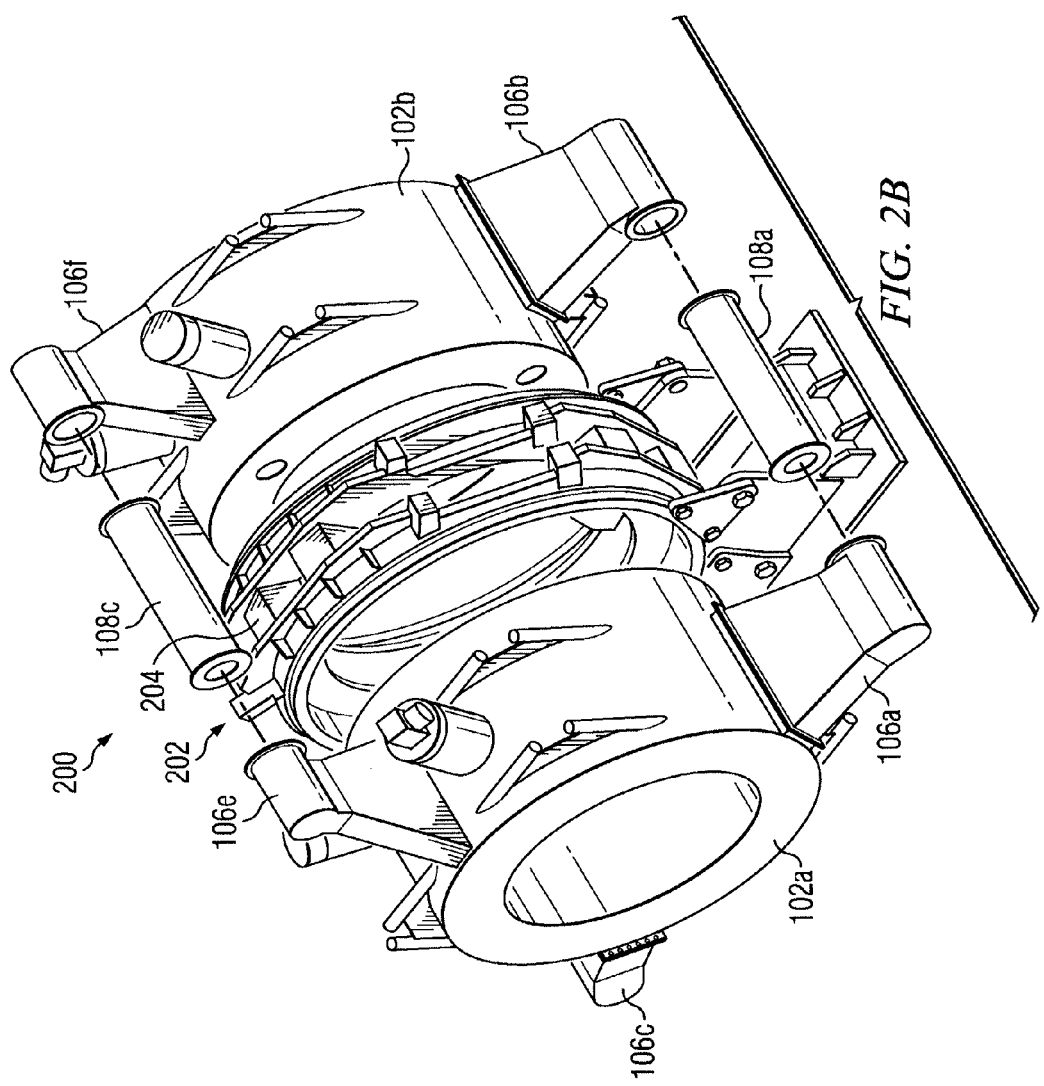

Referring now also to FIGS. 2A-2C, an alternative MRI system is shown as MRI system 200. MRI system 200 can include elements similar to those described in connection with MRI system 100, so like elements have retained like element numbers.

The MRI system 200 further includes a gantry 202 positioned in the gap 104. The gantry 202 can be used for supporting a radiation therapy device 204. The MRI system 200 can include, for example, a system that is capable of locating the anatomy of interest, imaging to develop a radiation treatment plan, and imaging during radiation treatment to correct the treatment application for patient motion. For example, the MRI system 200 can include a radiation source, such as a $Co^6$ radiation sources or linear electron accelerators (LINAC), supported by a gantry 202 as disclosed in U.S. Patent Application Publication 2005/0197564 to Dempsey, titled "System for Delivering Conformal Radiation Therapy While Simultaneously Imaging Soft Tissue," which is hereby incorporated herein by reference in its entirety, and/or as disclosed in U.S. Patent Application Publication 2011/0012593 to Shvartsman et al., titled "Method and Apparatus for Shielding a Linear Accelerator and a Magnetic Resonance Imaging Device From Each Other," which is hereby incorporated herein by reference in its entirety.

Thus, in some embodiments, the gantry 202 can be used for supporting a radiation therapy device 204 in the gap between the pair of MRI main magnets. A radiation therapy device 204 positioned in the gap can deliver radiation beams to a radiation therapy isocenter inside the imaging FOV without significant attenuation by the MRI magnets. The buttress assemblies 105a-105c can extend around the outside of the radiotherapy unit, clearing it so that there is no interference or obstruction of the radiotherapy beams. The gantry 202, MRI main magnet housings 102a and 102b, and buttress assemblies 105a-105c of the MRI system can be constructed to be capable of being disassembled for ease of installation into existing linear accelerator or cobalt therapy vaults designed for radiation therapy. In some embodiments, some or all of the buttress assemblies, or parts thereof, can be removable as described above in connection with FIGS. 1A-1C. For example, there can be n buttress assemblies, where n can be an integer greater than or equal to 2.

The buttress assemblies can have a cold connection or a room temperature separation support with axial suspension straps 206 to a cryostat. The cryostat can be slightly larger in diameter to include this suspension.

The source of radiation of the radiation therapy device 204 can be, for example, from an accelerator such as a LINAC or from a radioactive source such as Cobalt-60 ($^{60}Co$). The radiation can be delivered in uniform beams or modulated to tailor the radiation as required by the plan. This can include directing the beam, filtering the beam, turning the beam on and off, and shaping the beam with collimators. The imaging can take place simultaneously to the radiation delivery to allow for gating the beam on and off to prevent delivery during motion that would compromise the quality of delivery and to volumetrically record the delivery of the radiation dose to the patient's anatomy. It is desirable to direct the radiation to the patient without having interfering non-uniform radiation attenuating structures such as a magnet or gradient coils between the source and the patient. Prior MRI units with a central gap have not included a radiation treatment device and the support between their magnet halves was close to the imaging volume. One of the advantageous features of the disclosed MRI system is a superconducting MRI magnet with a central gap 104 to allow for radiation treatment. There have been proposals to pass the radiation beam through a magnet, but this is less desirable than a clear path from source to patient.

Figure 3:
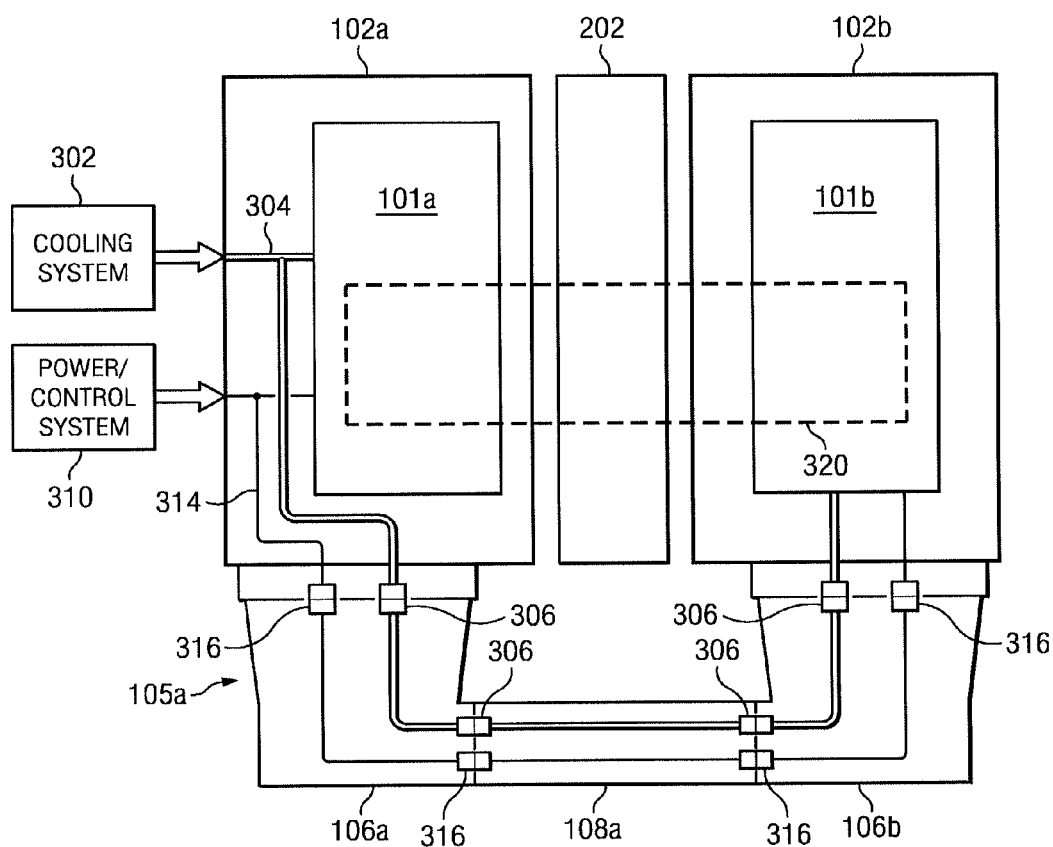
FIG. 3 shows a simplified block diagram of the split-magnet MRI systems disclosed herein.

Referring to FIG. 3, the disclosed MRI systems 100 and 200 can be configured in various embodiments where various conduits are routed through one or more of the buttress assemblies 105. For example, as shown in FIG. 3, the removable buttress assembly 105a can be used to house electrical and/or fluid conduit that extends between the first and second MRI magnet housings 102a and 102b. Various electrical and/or fluid conduits can additionally and/or alternatively be routed through buttress assembly 105b and/or 105c. It should be noted that while FIG. 3 shows MRI system 200, the description of FIG. 3 can apply equally to MRI system 100.

In some embodiments, the MRI system 200 can include a cooling system 302, which may include, for example, a cryostat. The cooling system 302 can include fluid conduit 304 that carries coolant for cooling the main MRI magnets 101a and 101b. The fluid conduit 304 can include a series of connectors 306, which can include any of a variety of known fluid-conduit connectors, at various locations at or near disassembly points of the buttress assembly 105a. This allows the fluid conduit 304 to be disconnected during the removal and disassembly of the buttress assembly 105a, and then later re-connected during the re-assembly of the buttress assembly 105a and re-connection of the buttress assembly 105a to the main MRI magnet housings 102a and 102b.

The MRI system 200 can also include a power/control system 310 that can encompass a variety of electrical and/or control systems, such as controlling the supply of electrical power to the main MRI magnets 101a and 101b during ramp up and ramp down of the MRI magnets 101a and 101b and/or communicating various other operational control signals with the main MRI magnets 101a and 101b. The power supply system 310 can include electrical conduit 314 that carries electricity and/or various control signals for powering and/or controlling the operation of the main MRI magnets 101a and 101b. The electrical conduit 314 can include a series of connectors 316, which can include any of a variety of known electrical connectors, at various locations at or near disassembly points of the buttress assembly 105a. This allows the conduit 314 to be disconnected during the removal and disassembly of the buttress assembly 105a, and then later re-connected during the re-assembly of the buttress assembly 105a and re-connection of the buttress assembly 105a to the main MRI magnet housings 102a and 102b.

In some embodiments, the power/control system 310 can include a single power supply that can be operated to provide electrical operating power to both of the main MRI magnets 101a and 101b. For example, the power/control system 310 can include a single power supply that can be operated to provide electrical power during ramp up and ramp down of the operations of the main MRI magnets 101a and 101b.

In prior systems, each MRI magnet receives electrical power from a respective power supply. During power-up, electrical power is ramped up to each of the MRI magnets most preferably in a simultaneous manner. However, often inhomogeneity in the main magnetic field of the MRI system is caused by differences in electric current to the respective main MRI magnets. Ideally, the electric current should be the same, or very close to the same, in the MRI magnets, so shimming is performed using shim coils that produce magnetic fields for correcting the inhomogeneity in the main magnetic field. In contrast, since the present MRI system provides electrical power to both MRI magnets 101a and 101b from a single power supply 310, the differences in electrical current to the two MRI magnets 101a and 101b is greatly reduced, thereby reducing the inhomogeneity in the main magnetic field of the MRI system as compared to prior MRI systems that separately powered each of the MRI magnets. As a result, the present MRI system can be more easily shimmed.

Embodiments of the MRI systems 100 and 200 can also include various configurations of RF and gradient coils, shown generally as coils 320. Specific examples and descriptions of coils 320 are disclosed in U.S. patent application Ser. No. 12/951,976 to Shvartsman et al., titled "Self-Shielded Gradient Coil," which is hereby incorporated herein by reference in its entirety. For example, the coils 320 can include gradient coils that include a gap aligned with gap 104 and gantry 202 for preventing attenuation of radiotherapy beams. The gradient coils also have a gap in the electronics to prevent attenuating the radiotherapy beam by conducting wires, but have a thin uniformly attenuating former to mechanically support the coils. The gradient coils also can have a gap in the electronics of the shield coils, but not the primary coils, to limit attenuating the radiotherapy beam by conducting wires, but can have a compensating material to produce uniform attenuation. The gradient coils can also have a gap in the electronics of the shield coils, but not the primary coils to limit attenuating the radiotherapy beam by conducting wires, but can have a compensating material to produce uniform attenuation and a conductor with a lower atomic number, such as Aluminum, to limit attenuation.

Preferably, the inside diameters of the main MRI magnets 101a and 101b allows for a radiation source of radiation therapy device 204 to be supported on the gantry 202 at a nominal radius of 1 m, which is the preferred distance for present radiation therapy treatment systems. The main MRI magnets 101a and 101b can be configured such that the radiotherapy beams emitted by the radiation therapy device 204 do not impinge on the main MRI magnets 101 a and 101 b on entrance to the MRI system, thereby preventing attenuation and degradation of the radiotherapy beam by scattering on the MRI coils 320. In some embodiments, the main MRI magnets 101a and 101b and the gradient coils 320 can be configured such that radiotherapy beams emitted by the radiation therapy device 204 do not impinge on the main MRI magnets 101a and 101b or the gradient coils 320 on entrance to the MRI system, preventing attenuation and degradation of the radiotherapy beam by scattering on the MRI coils 320 or the gradient system.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure.

Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A magnetic resonance imaging (MRI) system comprising:
    a first main MRI magnet disposed within a first MRI magnet housing;
    a second main MRI magnet disposed within a second MRI magnet housing separated by a gap from the first MRI magnet housing;
    a first plurality of buttress assemblies attached to an outer surface of the first MRI magnet housing, the first plurality of buttress assemblies configured to support the first MRI magnet housing;
    a second plurality of buttress assemblies attached to an outer surface of the second MRI magnet housing, the second plurality of buttress assemblies configured to support the second MRI magnet housing, and wherein at least one of the first and second plurality of buttress assemblies comprises an interior through which one or more conduits is routed; and
    a plurality of buttress connectors extending between the respective first and second plurality of buttress assemblies,
    wherein at least one of the first plurality of buttress assemblies is removably attached to the outer surface of the first MRI magnet housing and at least one of the second plurality of buttress assemblies is removably attached to the outer surface of the second MRI magnet housing.

2. The MRI system of claim 1, wherein each of the plurality of buttress connectors attaches to one of the first plurality of buttress assemblies and/or one of the second plurality of buttress assemblies.

3. The MRI system of claim 2, wherein each of the plurality of buttress connectors attaches to one of the first plurality of buttress assemblies and/or one of the second plurality of buttress assemblies by one or more removable connection devices.

4. The MRI system of claim 1, further comprising a gantry positioned in the gap.

5. The MRI system of claim 4, further comprising a radiation therapy device supported by the gantry.

6. The MRI system of claim 1, further comprising a cooling system, the cooling system including fluid conduit for carrying coolant for cooling the first and second main MRI magnets.

7. The MRI system of claim 6, wherein the fluid conduit extends from within the first MRI magnet housing to within the second MRI magnet housing by routing through the interior of the at least one of the first plurality of buttress assemblies and routing through the interior of the at least one of the second plurality of buttress assemblies.

8. The MRI system of claim 1, further comprising a power system, the power system including electrical conduit for providing electrical power to the first and second main MRI magnets.

9. The MRI system of claim 8, wherein the electrical conduit extends from within the first MRI magnet housing to within the second MRI magnet housing by routing through the interior of the at least one of the first plurality of buttress assemblies and routing through the interior of the at least one of the second plurality of buttress assemblies.

10. The MRI system of claim 8, wherein the first and second MRI magnet housings are separated along a longitudinal axis of the system and wherein the first and second main MRI magnets are disposed about the longitudinal axis.

11. The MRI system of claim 1, wherein the first and second MRI magnet housings are substantially cylindrical such that a patient bed of the system extends through a center of the first and second MRI housings.

12. A magnetic resonance imaging (MRI) system comprising:
    a first main MRI magnet surrounded by a first MRI magnet housing;
    a second main MRI magnet surrounded by a second MRI magnet housing and separated from the first MRI magnet housing by a MRI magnet gap;
    a first buttress assembly removably attached to an outer surface of the first MRI magnet housing;
    a second buttress assembly removably attached to the first buttress assembly and removably attached to an outer surface of the second MRI magnet housings; and
    a cooling system including a fluid conduit for carrying coolant for cooling the first and second main MRI magnets that routes through an interior of at least one of the first and second buttress assemblies.

13. The MRI system of claim 12, wherein the second buttress assembly is removably attached to the first buttress assembly by a buttress connector that is removably attached to the first and second buttress assemblies.

14. The MRI system of claim 13, wherein the fluid conduit extends from within the first MRI magnet housing to within the second MRI magnet housing by routing through an interior of the first buttress assembly, the second buttress assembly and the buttress connector.

15. The MRI system of claim 14, wherein the fluid conduit has a connector positioned near one or more disassembly points of the first buttress assembly and near one or more disassembly points of the second buttress assembly.

16. The MRI system of claim 12, further comprising a power system, the power system including electrical conduit for providing electrical power to the first and second main MRI magnets.

17. The MRI system of claim 16, wherein the electrical conduit extends from within the first MRI magnet housing to within the second MRI magnet housing by routing through an interior of at least one of the removably attached buttress assemblies.

18. The MRI system of claim 12, wherein the first and second MRI magnet housings are substantially cylindrical such that a patient bed of the system extends through a center of the first and second MRI housings.

19. The MRI system of claim 12, wherein the first buttress assembly extends radially from the outer surface of the first MRI magnet housing, and the second buttress assembly extends radially from the outer surface of the second MRI magnet housing.

20. The MRI system of claim 12, further comprising a gantry positioned in the MRI magnet gap and a radiation therapy device supported by the gantry.

* * * * *